United States Patent
Murakoshi

(10) Patent No.: US 11,040,263 B2
(45) Date of Patent: Jun. 22, 2021

(54) SENSING SYSTEM, SENSOR DEVICE, AND SENSOR FIXTURE

(71) Applicant: SONY CORPORATION, Tokyo (JP)

(72) Inventor: Sho Murakoshi, Tokyo (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 15/751,054

(22) PCT Filed: Jul. 26, 2016

(86) PCT No.: PCT/JP2016/071848
§ 371 (c)(1),
(2) Date: Feb. 7, 2018

(87) PCT Pub. No.: WO2017/056661
PCT Pub. Date: Apr. 6, 2017

(65) Prior Publication Data
US 2018/0236340 A1  Aug. 23, 2018

(30) Foreign Application Priority Data

Sep. 29, 2015 (JP) .............................. JP2015-191864

(51) Int. Cl.
*A63B 69/36* (2006.01)
*H04Q 9/00* (2006.01)
(Continued)

(52) U.S. Cl.
CPC ........ *A63B 69/3658* (2013.01); *A61B 5/1122* (2013.01); *A61B 5/6895* (2013.01);
(Continued)

(58) Field of Classification Search
CPC . A63B 69/3658; A63B 69/3632; A63B 69/38; A61B 5/1122; A61B 5/6895;
(Continued)

(56) References Cited

U.S. PATENT DOCUMENTS 7,727,080 B1 * 6/2010 Fitzgerald .......... A63B 69/3632
473/221
8,672,779 B1   3/2014 Sakyo et al.
(Continued)

FOREIGN PATENT DOCUMENTS

CA    2848361 A    3/2013
CN   105228707 A   1/2016
(Continued)

OTHER PUBLICATIONS

International Search Report and Written Opinion of PCT Application No. PCT/JP2016/071848, dated Sep. 6, 2016, 10 pages.

*Primary Examiner* — Dmitry Suhol
*Assistant Examiner* — Carl V Larsen
(74) *Attorney, Agent, or Firm* — Chip Law Group

(57) ABSTRACT

Provided is a sensing system, a sensor device, and a sensor fixture. The sensing system includes a sensor fixture that has a mode corresponding to an attachment attitude to a target object and a sensor device that is attachable with the attachment attitude to the target object via the sensor fixture. The sensor device includes a sensor unit that senses information regarding the target object, and an acquisition unit that acquires information indicating the attachment attitude based on the mode of the sensor fixture.

12 Claims, 9 Drawing Sheets

(51) Int. Cl.
| | |
|---|---|
| *G06K 9/00* | (2006.01) |
| *G06Q 10/06* | (2012.01) |
| *A61B 5/00* | (2006.01) |
| *A61B 5/11* | (2006.01) |
| *G09B 19/00* | (2006.01) |
| *A63B 69/38* | (2006.01) |
| *G08C 17/00* | (2006.01) |

(52) U.S. Cl.
CPC .......... *A63B 69/38* (2013.01); *G06K 9/00342* (2013.01); *G06Q 10/0639* (2013.01); *G08C 17/00* (2013.01); *G09B 19/0038* (2013.01); *H04Q 9/00* (2013.01); *A61B 2503/10* (2013.01); *A61B 2505/09* (2013.01); *A61B 2562/0219* (2013.01); *A63B 2220/40* (2013.01); *A63B 2220/80* (2013.01); *H04Q 2209/40* (2013.01)

(58) Field of Classification Search
CPC ........ A61B 2562/0219; G06K 9/00342; A63F 13/56; G06Q 10/0639; G09B 19/0038; G08C 17/00
See application file for complete search history.

(56) References Cited

U.S. PATENT DOCUMENTS

| | | | | |
|---|---|---|---|---|
| 8,696,482 | B1* | 4/2014 | Pedenko | A63B 69/3632 473/221 |
| 8,986,130 | B2 | 3/2015 | Hatton et al. | |
| 2006/0052173 | A1 | 3/2006 | Telford | |
| 2006/0084516 | A1 | 4/2006 | Eyestone et al. | |
| 2007/0206837 | A1* | 9/2007 | Kirby | A63B 24/0003 382/107 |
| 2009/0058663 | A1* | 3/2009 | Joshi | G01D 11/24 340/584 |
| 2009/0247312 | A1 | 10/2009 | Sato et al. | |
| 2011/0203954 | A1* | 8/2011 | Kroupa | B65H 75/4431 206/320 |
| 2012/0157241 | A1* | 6/2012 | Nomura | A63B 69/0002 473/422 |
| 2013/0065703 | A1 | 3/2013 | Rose | |
| 2013/0267335 | A1* | 10/2013 | Boyd | A63B 69/36 473/222 |
| 2014/0228141 | A1 | 8/2014 | Sakyo et al. | |
| 2014/0379294 | A1* | 12/2014 | Shibuya | G01P 7/00 702/141 |
| 2015/0283428 | A1 | 10/2015 | Shibuya et al. | |
| 2016/0166880 | A1* | 6/2016 | Nakajima | A61B 5/743 434/247 |
| 2016/0335557 | A1* | 11/2016 | Kurata | G06F 1/1626 |
| 2017/0001070 | A1* | 1/2017 | Zhao | A63B 51/00 |
| 2017/0106240 | A1* | 4/2017 | Chuang | A63B 21/0726 |
| 2017/0234706 | A1* | 8/2017 | Martin | G01D 11/245 29/407.05 |
| 2017/0287147 | A1* | 10/2017 | Takahashi | G06K 9/00771 |
| 2017/0354844 | A1* | 12/2017 | Nomura | A63B 69/36 |
| 2018/0050254 | A1* | 2/2018 | Maani | G06K 9/00523 |
| 2018/0050255 | A1* | 2/2018 | Maani | G06K 9/00342 |

FOREIGN PATENT DOCUMENTS

| | | |
|---|---|---|
| EP | 2756419 A1 | 7/2014 |
| EP | 2858726 A1 | 4/2015 |
| JP | 2009-240677 A | 10/2009 |
| JP | 2012-200540 A | 10/2009 |
| JP | 2012-200540 A | 10/2012 |
| JP | 2014-100341 A | 6/2014 |
| JP | 2014-155587 A | 8/2014 |
| JP | 2015-517887 A | 6/2015 |
| JP | 2016-515891 A | 6/2016 |
| WO | 2013/039959 A1 | 3/2013 |
| WO | 2013/181561 A1 | 12/2013 |
| WO | 2014/125790 A1 | 8/2014 |

* cited by examiner

SENSING SYSTEM, SENSOR DEVICE, AND SENSOR FIXTURE

CROSS REFERENCE TO RELATED APPLICATIONS

This application is a U.S. National Phase of International Patent Application No. PCT/JP2016/071848 filed on Jul. 26, 2016, which claims priority benefit of Japanese Patent Application No. JP 2015-191864 filed in the Japan Patent Office on Sep. 29, 2015. Each of the above-referenced applications is hereby incorporated herein by reference in its entirety.

TECHNICAL FIELD

The present disclosure relates to sensing systems, sensor devices, and sensor fixtures.

BACKGROUND ART

In recent years, attempts to apply information process technologies have been made in various fields. For example, there are technologies of visualizing movement of players in sports fields. The player measures and records movement of his/her body or a sports implement by using various kinds of sensor devices, and it is possible to check whether the player has smoothly made movement that suits the sports. Therefore, the player can improve his/her form and the like with reference to the visualized movement.

Technologies of visualizing the body's movement have various approaches including motion capture. In one example, Patent Literature 1 listed below discloses a technology of measuring the acceleration by an acceleration sensor mounted on the hand of a player and calculating the speed of the tip of a sports implement that the player swings, on the basis of the measurement result.

CITATION LIST

Patent Literature

Patent Literature 1: JP 2012-200540A

DISCLOSURE OF INVENTION

Technical Problem

However, sometimes it may be difficult to appropriately visualize the movement by using the technology described in the above-listed Patent Literature 1 in the case where the sensor is not attached with a specific attachment attitude to a measurement target object (hand of a player). For example, preferable attachment attitudes are different depending on types of sports. Therefore, it is preferable to take measurements corresponding to various types of attachment attitudes.

Therefore, the present disclosure proposes a novel and improved sensing system, sensor device, and sensor fixture that are capable of taking measurements corresponding to various types of attachment attitudes.

Solution to Problem

According to the present disclosure, there is provide a sensing system including: a sensor fixture that has a mode corresponding to an attachment attitude to a target object; and a sensor device configured to be attached with the attachment attitude to the target object via the sensor fixture, the sensor device including a sensor unit configured to sense information regarding the target object, and an acquisition unit configured to acquire information indicating the attachment attitude on a basis of the mode of the sensor fixture.

In addition, according to the present disclosure, there is provided a sensor device including: a sensor unit configured to sense information regarding a target object; and an acquisition unit configured to acquire information indicating attachment attitude to the target object, from a sensor fixture. The sensor device is configured to be attached with the attachment attitude to the target object via the sensor fixture.

In addition, according to the present disclosure, there is provided a sensor fixture that has a mode corresponding to an attachment attitude to a target object, and that attaches a sensor device with the attachment attitude to the target object.

Advantageous Effects of Invention

As described above, according to the present disclosure, it is possible to take measurements corresponding to various kinds of attachment attitudes.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
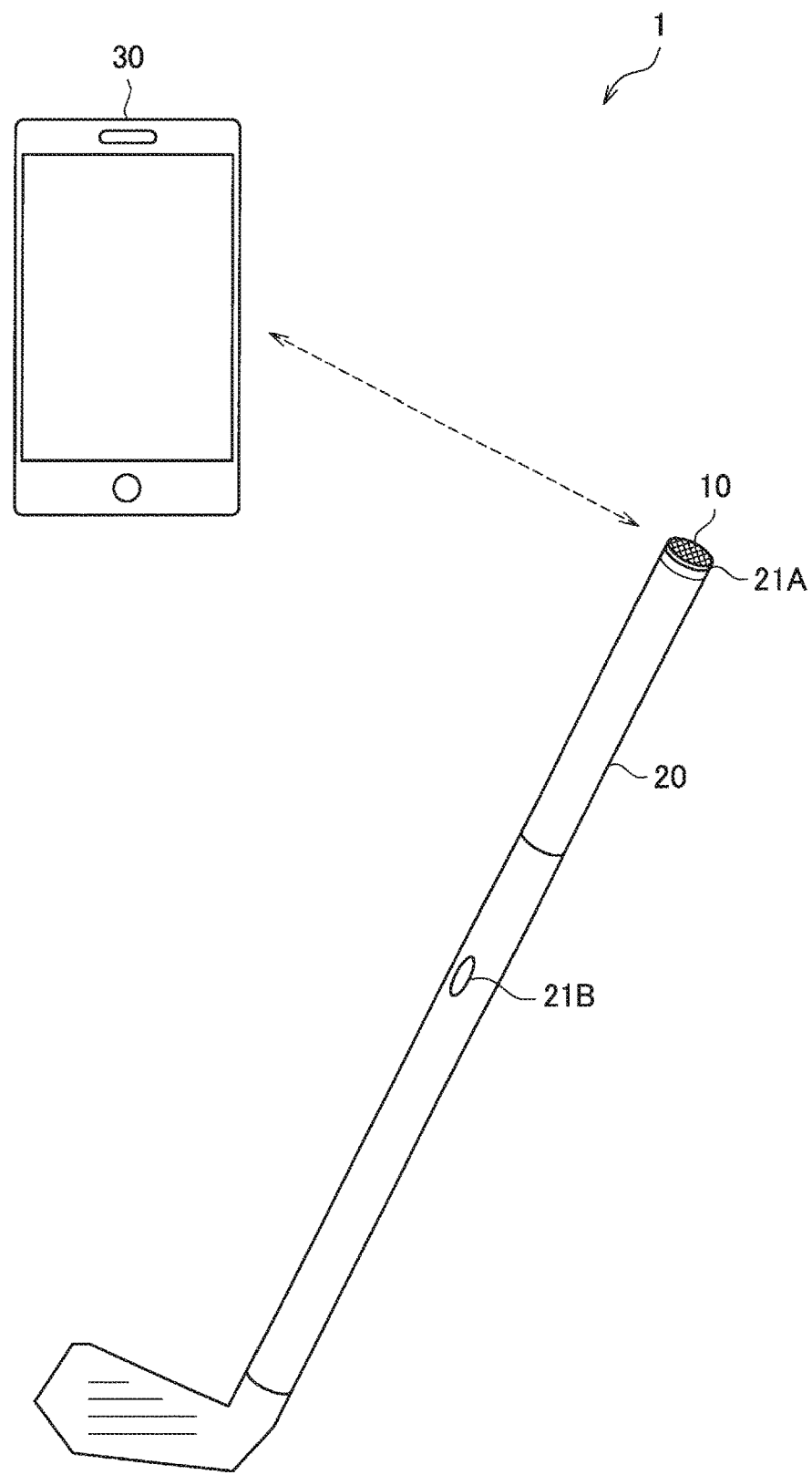
FIG. 1 is an explanatory diagram illustrating an overview of a sensing system 1 according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, there is a case in which structural elements having substantially the same function are discriminated by affixing different alphabets after the same reference numeral in the present specification and drawings. In one example, structural elements having substantially the same functional configuration are discriminated as sensor devices 10A, 10B, and 10C as necessary. However, when there is no need to discriminate particularly between a plurality of structural elements having substantially the same functional configuration, only the same reference numeral is affixed. In one example, in the case where there is no need to discriminate particularly between the sensor devices 10A, 10B, and 10C, these sensor devices are simply referred to as sensor devices 10.

<<1. Overview>>
<1-1. Overall configuration>
<1-2. Background>
<<2. Configuration example>>
<2-1. External configuration example of sensor device>
<2-2. Functional configuration example of sensor device>
<2-3. Functional configuration example of smartphone>
<<2. Operation Example>>
<<4. Modifications>>
<4-1. First modification>
<4-2. Second modification>
<<5. Hardware configuration example>
<<6. Conclusion>>

1. OVERVIEW

1-1. Overall Configuration>

First, an overview of a sensing system according to an embodiment of the present disclosure will be described with reference to FIG. 1.

FIG. 1 is an explanatory diagram illustrating an overview of a sensing system 1 according to the embodiment. As illustrated in FIG. 1, the sensing system 1 includes one or more sensor devices 10 that are attached to a target object 20, and an information processing device 30.

The sensor device 10 is a device for sensing various kinds of data. The sensor device 10 is attached to the target object 20 via a sensor fixture 21A or a sensor fixture 21 B that are installed on the target object 20, and the sensor device 10 senses movement of the target object 20. The sensor device 10 establishes a wireless connection with the information processing device 30, and transmits acquired data to the information processing device 30 or receives an instruction from the information processing device 30.

The sensor device 10 is capable of measuring various kinds of data by alone or in combination with another sensor device 10. The sensor device 10 includes an inertia sensor such as a triaxial acceleration sensor and a triaxial gyro sensor (for example, x axis, y axis, and z axis). In such a case, it is possible to obtain a trajectory of movement of the target object 20, a speed of the movement, and the like from a result of sensing (sensor information) performed by the sensor device 10. Note that, a process of calculating such information from sensor information can be performed by, in one example, the information processing device 30.

The target object 20 is an object that is subjected to sensing performed by the sensor device 10. The target object 20 may be an object to be used by a living being. For example, the target object 20 may be equipment used in sports such as a golf club, a tennis racket, a ball, a ski, a ski boot, a goal, or a bat. In addition, the target object 20 may be equipment or transportation used for daily life such as a prosthetic hand, a wheel chair, a bicycle, or a car. In addition, the target object 20 may be equipment used for an animal such as a collar or a horseshoe.

As illustrated in FIG. 1, the target object 20 has one or more attachment positions (sensor fixtures 21) to which the sensor device 10 is detachably attached. It is possible to attach the sensor device 10 to one or all attachment positions. The sensor fixture 21 may be installed on the target object 20 when manufacturing the target object 20, or may be installed on the target object 20 after manufacturing the target object 20. For example, the sensor fixture 21 may be integrated with an object (target object 20) such as a golf club, a tennis racket, or a ski, or may be attached to the target object 20. In the case where the target object 20 includes a plurality of sensor fixtures 21, it is possible for a user to attach the sensor device 10 to the target object 20 via any sensor fixture 21. In addition, it is also possible for the user to attach the plurality of sensor devices 10 to the target object 20 at any attachment positions. Therefore, flexible measurement can be achieved.

The information processing device 30 is a device configured to process information output from the sensor device 10. The information processing device 30 can be implemented as a smartphone, a tablet terminal, a PC, a server, or the like. In the example illustrated in FIG. 1, the information processing device 30 is a smartphone. In one example, the smartphone 30 visualizes and displays sensor information acquired by the sensor device 10, to feed the visualized information back to the user, or to provide various services such as advice or product recommendation for improving sports ability.

The communication network 5 is a wired or wireless transmission path through which information is transmitted from devices connected with the communication network 5. For example, the communication network 5 may include a public network, various kinds of local area networks (LANs), a wide area network (WAN), and the like. The public network includes the Internet, a satellite communication network, a telephone network, and the like, and the LANs include Ethernet (registered trademark). In addition, the communication network 5 may include a dedicated line network such as an Internet Protocol Virtual Private Network (IP-VPN).

1-2. Background

The overall configuration example of the sensing system 1 according to the embodiment of the present disclosure has been described above. Next, background of the invention of the sensing system 1 according to the embodiment will be described.

Figure 2:
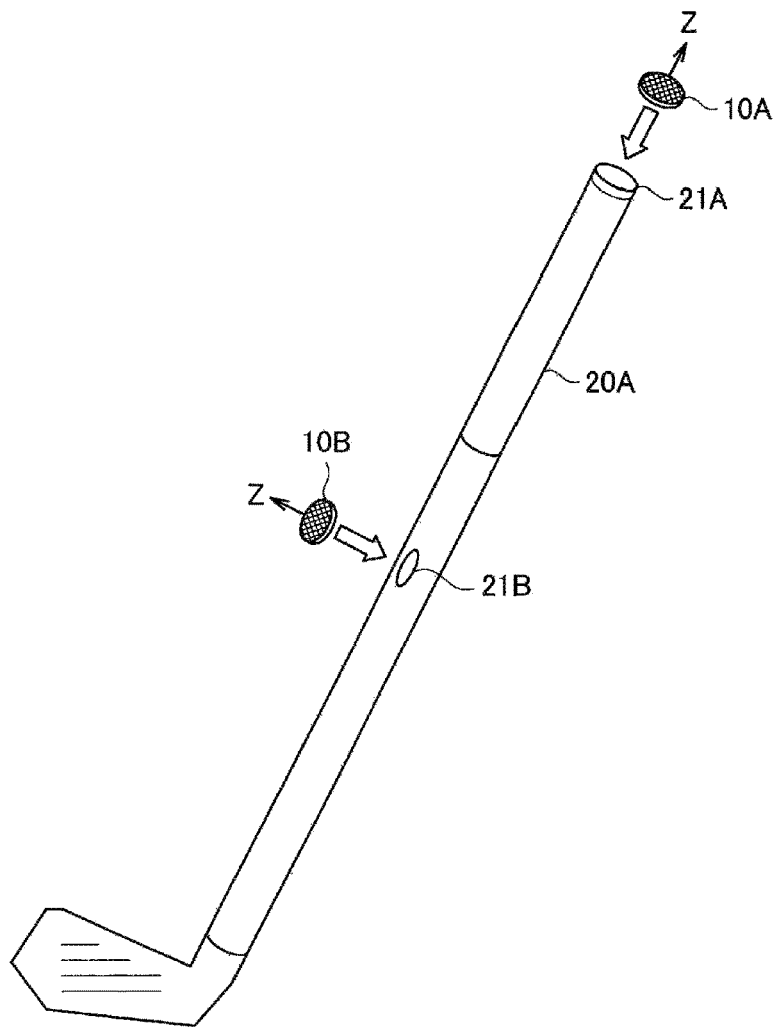
FIG. 2 is an explanatory diagram illustrating ways of attaching a plurality of sensor devices.

In recent years, various kinds of sensors have getting smaller, and degrees of freedom of attachment of sensors have been increased. The example in which the sensor device 10 is attached to the target object 20 via the sensor fixture 21A has been described above. However, as illustrated in FIG. 1, the target object 20 may include the plurality of sensor fixtures 21 (sensor attachment positions), and it is possible for a user to attach the sensor device 10 via any sensor fixture 21. Next, with reference to FIG. 2 and FIG. 3, ways of attaching sensors to a target object will be described. FIG. 2 is an explanatory diagram illustrating ways of attaching a plurality of sensor devices.

As illustrated in FIG. 2, there are two ways of attaching the sensor device 10 to a golf club 20A serving as the target object. Like the sensor device 10A, the sensor device 10 may be attached via the sensor fixture 21A installed on a grip. Alternatively, like the sensor device 10B, the sensor device 10 may be attached via a sensor fixture 21B installed on a shaft. As illustrated in FIG. 2, in the case where the sensor device 10A is attached via the sensor fixture 21A, the z axis of the sensor device 10A is in a direction along the shaft of the golf club 20A. On the other hand, as illustrated in FIG. 2, in the case where the sensor device 10B is attached via the sensor fixture 21B, the z axis of the sensor device 10B is in a direction perpendicular to the shaft of the golf club 20A. As described above, the axes of the sensor device 10 have different relations (attachment attitudes) with the target object in accordance with the attachment position of the sensor device 10 and the way of attaching the sensor device 10.

As described above, it is possible to attach the sensor devices 10 at the plurality of attachment positions and with a plurality of attachment attitudes. Therefore, it is possible for the user to change ways of attaching the sensor device in accordance with types or magnitude of movement (such as golf swing) that the user wants to measure and visualize. For example, in the case of visualizing movement of a part close to a hand, the sensor device 10 may be attached via the sensor fixture 21A. In the case of visualizing movement at a position close to a ball impact point, the sensor device 10 may be attached via the sensor fixture 21B. In addition, in some cases, the triaxial inertia sensor may have axes with different accuracies. Therefore, it may be considered that the way of attaching the sensor device is changed to obtain an attachment attitude such that a direction of fine movement does not match an axis with low accuracy in the case of measuring fine movement.

In addition, in the case of a user having a plurality of target objects, it is a bother for him/her to prepare the same number of sensors as the number of the target objects. Therefore, it is desired to use the sensor device 10 for measuring both movement of a certain target object and movement of another target object. However, in some cases, an attachment attitude may be decided in accordance with a type of a target object to which the sensor device 10 is attached.

Figure 3:
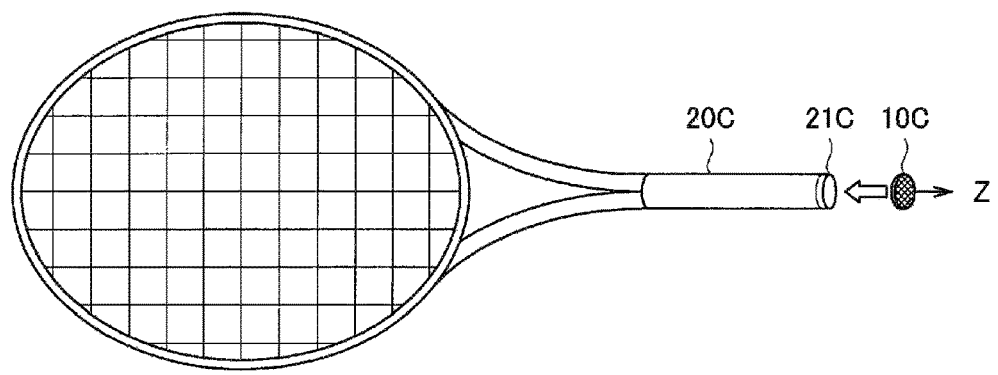
FIG. 3 is an explanatory diagram illustrating another example of a way of attaching a sensor device to a target object.

FIG. 3 is an explanatory diagram illustrating another example of a way of attaching a sensor device to a target object. As illustrated in FIG. 3, for example, there may be only one way of attaching the sensor device 10 to a tennis racket 20C serving as a target object because of its size and structure. For example, like the sensor device 10C illustrated in FIG. 3, the sensor device 10 may be attached via a sensor fixture 21C installed on a grip. In this case, the z axis of the sensor device 10C is in a direction along the shaft of the tennis racket 20C.

As described above, the axes of the sensor device 10 have different relations (attachment attitudes) with the target object in accordance with ways of attaching the sensor device 10 and target objects to which the sensor device 10 is attached. In the case where the relation) between the target object and axes of the sensor device 10 is not fixed, it is difficult to set appropriate coordinate axes for visualization.

For example, it is possible to set one axis (such as z axis) for visualization by specifying a gravitational acceleration direction in a still state. However, the rest two axes (such as x axis and y axis) vary depending on attachment attitudes (for example, the x axis switches its places with the y axis, or a positive direction of an axis switches with a negative direction of the axis). Therefore, the same movements or substantially the same movements may be visualized as if they are different from each other.

Note that, in the case where the sensor device 10 includes a magnetic sensor, the rest two axes may be set on the basis of cardinal directions. However, the magnetic sensor is affected by metal. Therefore, sometimes the magnetic sensor cannot acquire a correct cardinal direction and therefore it is difficult to set the rest two axes appropriately.

Figure 4:
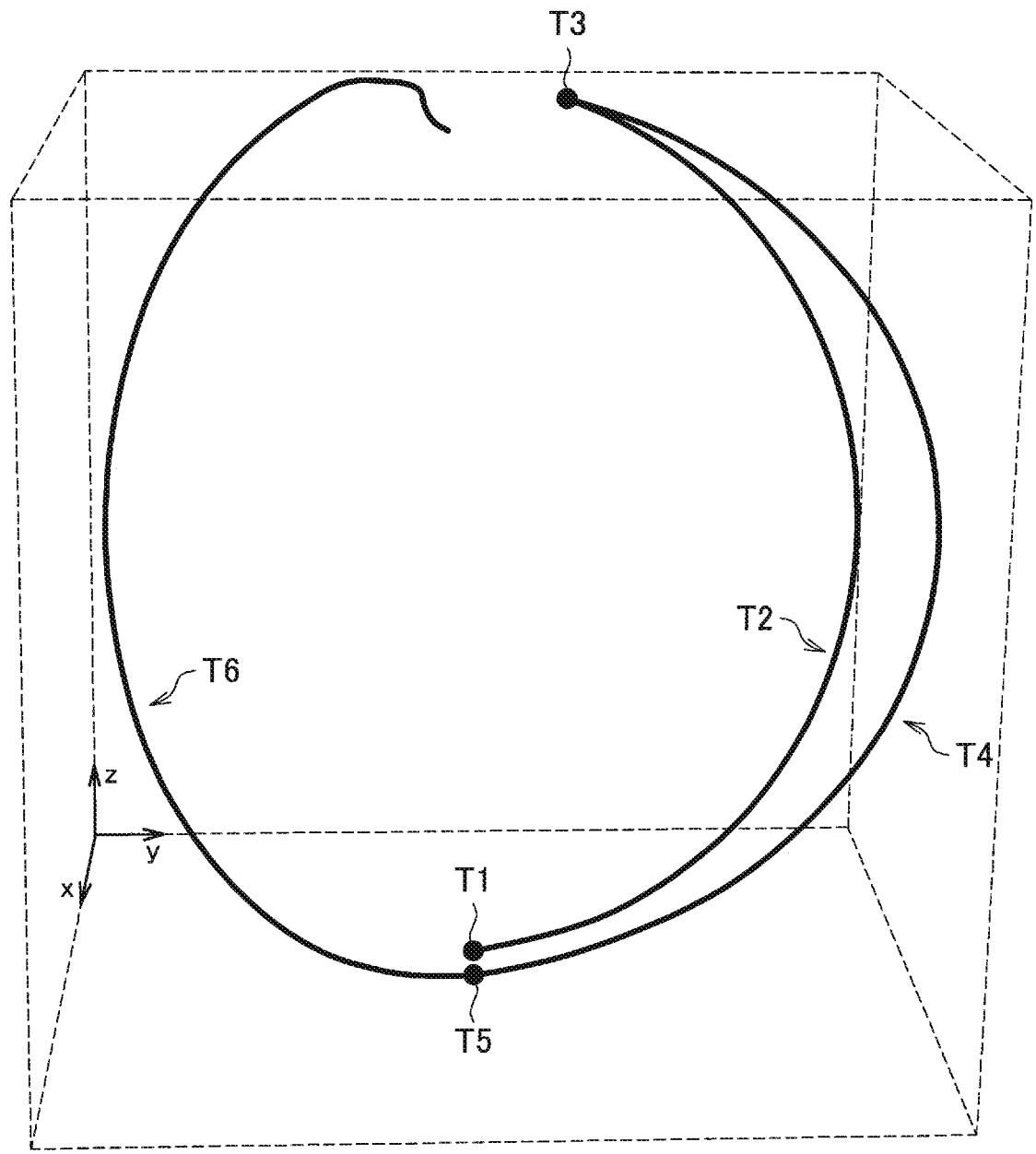
FIG. 4 is an explanatory diagram illustrating a display example in which sensor information is visualized as a trajectory of movement of a target object.
Figure 5:
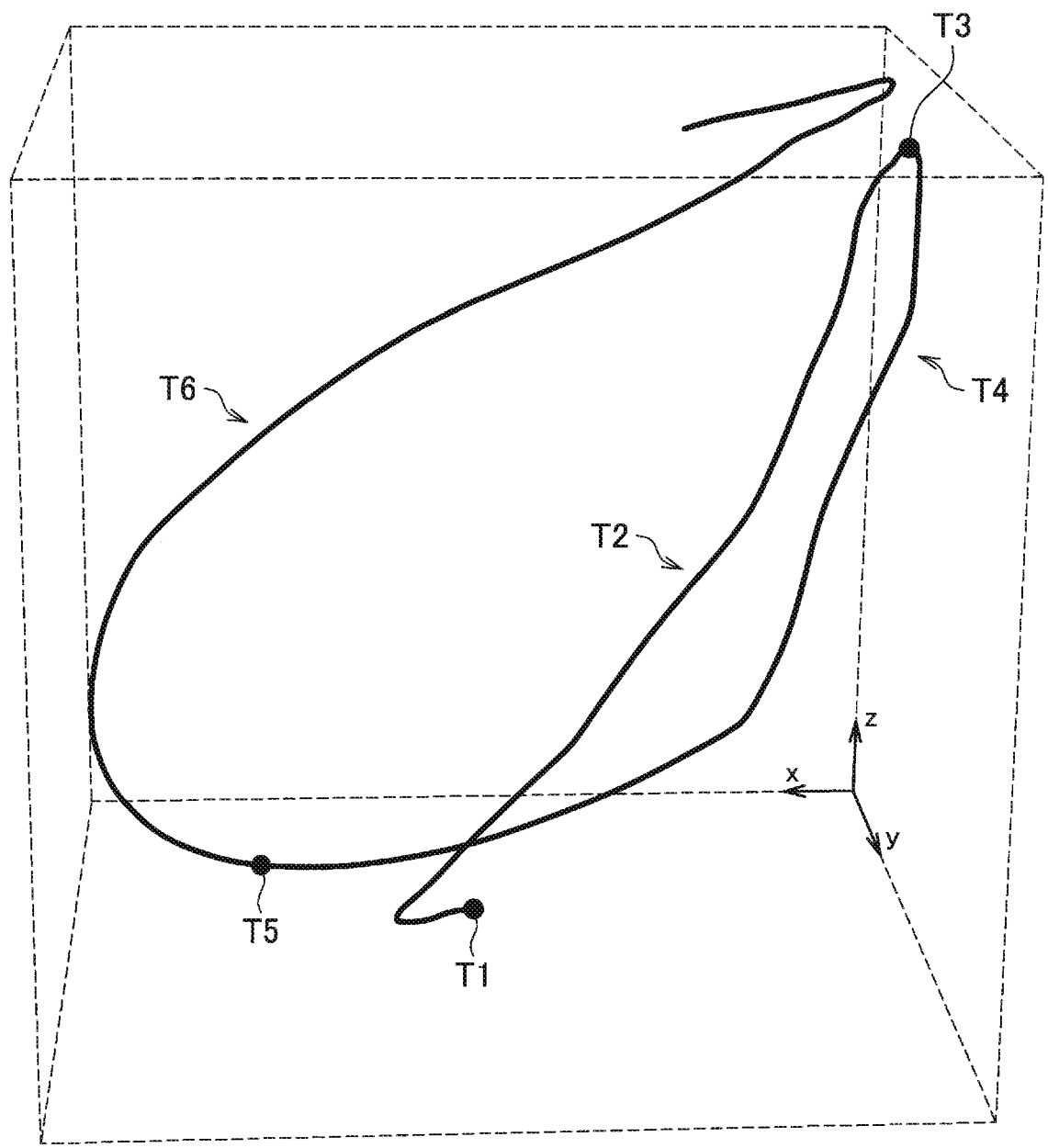
FIG. 5 is an explanatory diagram illustrating a display example in which sensor information is visualized as a trajectory of movement of a target object.
Figure 6:
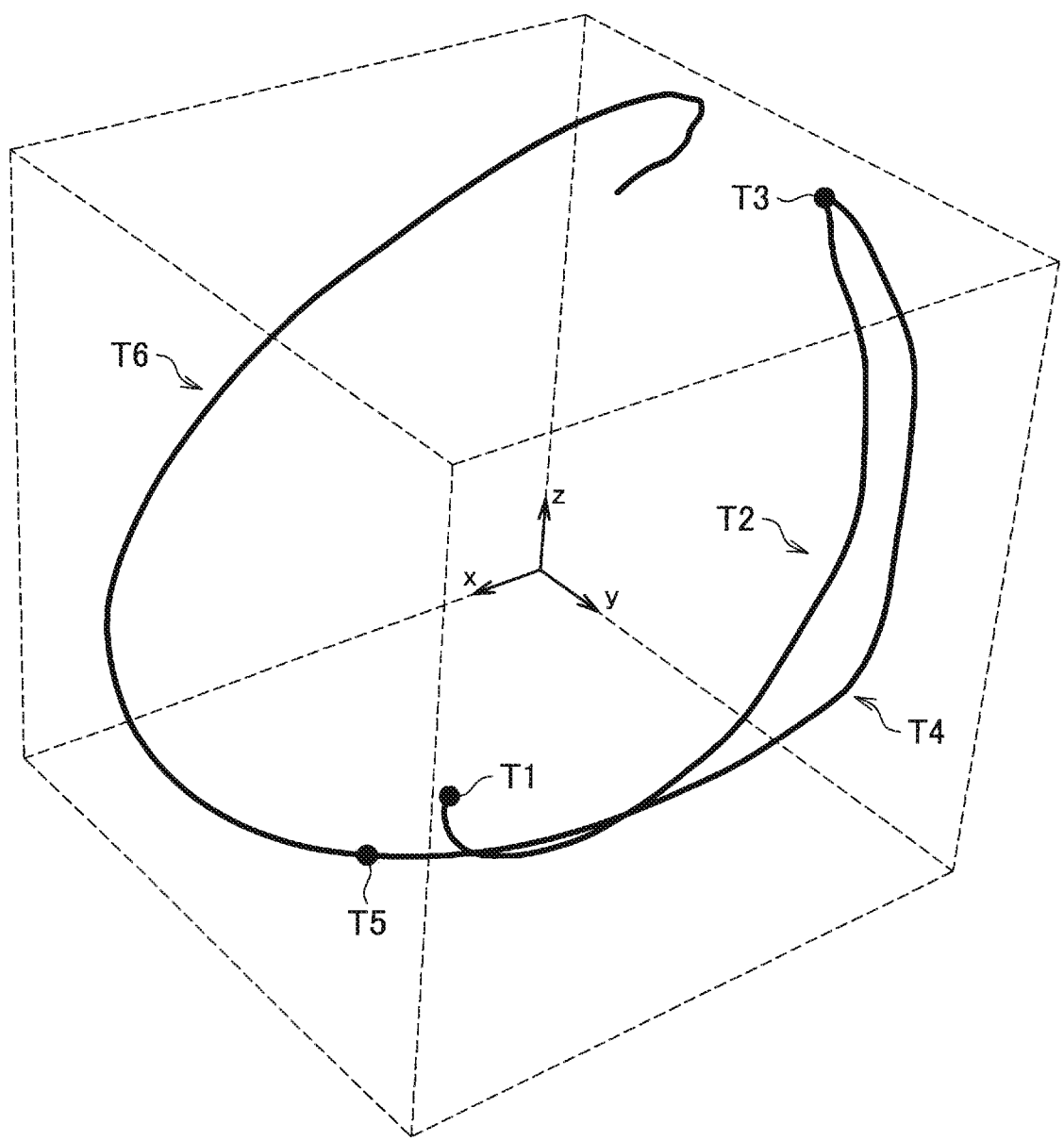
FIG. 6 is an explanatory diagram illustrating a display example in which sensor information is visualized as a trajectory of movement of a target object.

Next, with reference to FIG. 4 to FIG. 6, relations between attachment attitudes and visualization will be described. FIG. 4 to FIG. 6 are explanatory diagrams illustrating display examples in which pieces of sensor information acquired by sensor devices 10 attached with different attachment attitudes to a target object (golf club) are visualized as trajectories of movement of the target object. The display examples in FIG. 4 to FIG. 6 are displayed on the smartphone 30 described with reference to FIG. 1, for example.

FIG. 4 illustrates a display example in which swing (movement of the target object) is appropriately visualized. In addition, FIG. 5 and FIG. 6 illustrate display examples in which substantially the same swings as the example in FIG. 4 are appropriately visualized on the basis of sensor information acquired by sensor devices 10 that are attached with different attachment attitudes to the target object in comparison with the example in FIG. 4. FIG. 4 to FIG. 6 visualizes trajectories of movement regarding golf swing. A point T1 represents address, a section T2 represents backswing movement, a point T3 represents a top of the backswing, a section T4 represents downswing movement, a section T5 represents impact, and a section T6 represents follow through movement. Note that, the coordinate axes (x, y, and z) in FIG. 4 to FIG. 6 are illustrated merely for descriptive purposes to show difference between attachment attitudes.

Here, FIG. 4 visualizes sensor information from a front direction of a user making golf swing, and the user can easily recognize a trajectory of movement regarding the golf swing. However, FIG. 5 and FIG. 6 show trajectories that seem to be different from FIG. 4 because of different attachment attitudes from the example in FIG. 4. Therefore, it is difficult for the user to check whether he/she has made smooth movement regarding the golf swing. In addition, it is also difficult for the user to compare the trajectories illustrated in FIG. 4 to FIG. 6. Therefore, it is also difficult to utilize the trajectories to improve his/her golf swing form or the like, for example.

To appropriately visualize sensor information acquired in the examples illustrated in FIG. 5 and FIG. 6 like FIG. 4, it is only necessary to perform a process of rotating the sensor information in accordance with a relation between the target object and axes of the sensor devices 10 (attachment attitudes), for example.

Therefore, the sensing system 1 according to the embodiment of the present disclosure has been developed in view of the above described circumstances. The sensing system 1 according to the embodiment is capable of specifying attachment attitudes of the sensor devices 10, and performing processes corresponding to the attachment attitudes. Next, details of the configurations according to the embodiment having such effects will be described.

2. CONFIGURATION EXAMPLE

Configuration examples of respective devices included in the sensing system 1 according to the embodiment will be described below one by one with reference to FIGS. 7 to 10.

2-1. External Configuration Examples of Sensor Device and Sensor Fixture

Figure 7:
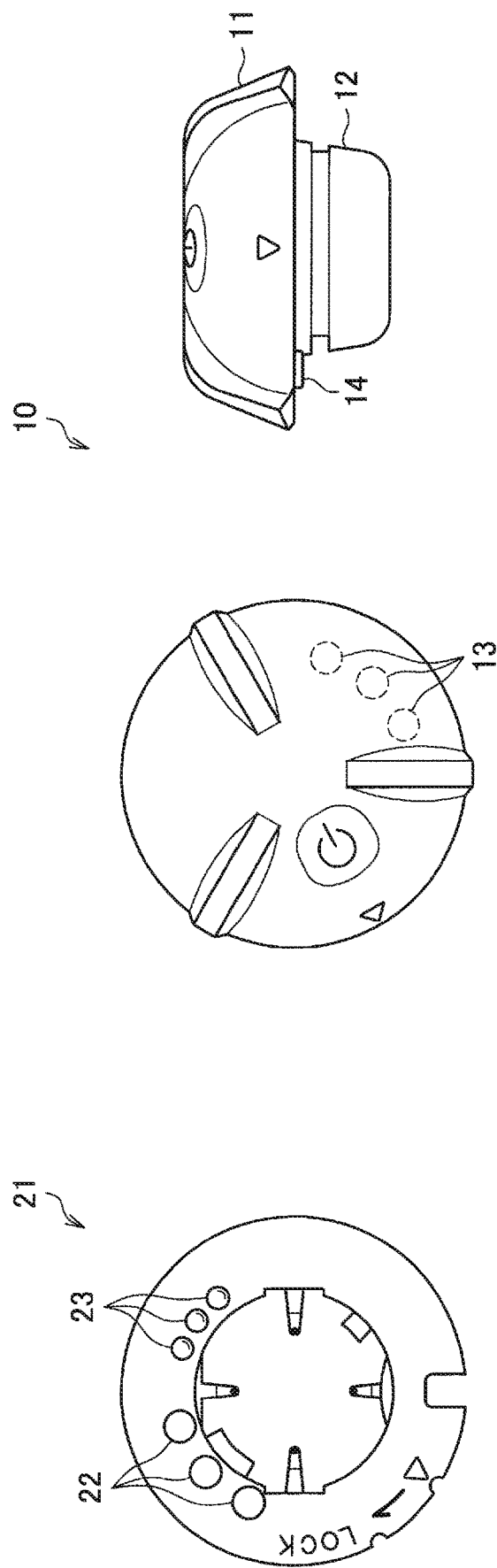
FIG. 7 is a diagram illustrating an example of an external configuration of a sensor device 10 and a sensor fixture 10 according to the embodiment.

FIG. 7 is a diagram illustrating an example of an external configuration of the sensor device 10 and the sensor fixture 21 according to the embodiment. As illustrated in FIG. 7, the sensor device 10 includes a main body portion 11 and an attachment portion 12. The main body portion 11 includes, in one example, a sensor. The attachment portion 12 is detachably attached to any of one or more sensor fixtures 21 included in the target object. In one example, the attachment portion 12 has a groove along a surface of a cylinder and is screwed into the sensor fixture 21. This structure allows the sensor device to be attached with a predetermined attachment attitude to the target object 20 via the sensor fixture 21.

The sensor device 10 is provided with a terminal 13. The sensor fixture 21 is also provided with a terminal 22. In one example, when the sensor device 10 is attached to the sensor fixture 21, the terminal 13 and the terminal 22 are in contact with each other, and electric signals can be exchanged.

The sensor device 10 is provided with a switch 14. The sensor fixture 21 is provided with a concavo-convex portion 23. In one example, when the sensor device 10 is screwed into the sensor fixture 21, convex portions of the concavo-convex portion 23 sequentially press the switch 14. In the example illustrated in FIG. 7, the three convex portions of the concavo-convex portion 23 are aligned at equal intervals in an arc-shaped row along the trajectory of the switch 14 so that the convex portions sequentially press the switch 14 when the sensor device 10 is screwed into the sensor fixture 21. However, the present technology is not limited to this example. In one example, the number of convex portions may be optional, and the convex portions may be aligned at optional intervals in a plurality of rows. Note that, in the case where the convex portions are provided in a plurality of rows, it is preferable that the switch 14 is also provided in a plurality of rows.

The sensor fixture 21 has modes corresponding to attachment attitudes of the sensor device 10 to the target object 20, for example. In addition, the sensor fixture 21 may have modes corresponding to attachment positions on the target object 20. Since the sensor fixture 21 has modes corresponding to the attachment attitudes and the attachment positions as described above, it is possible for the sensor device 10 to acquire information indicating an attachment attitude and information indicating an attachment position.

2.2. Functional Configuration Example of Sensor Device

Figure 8:
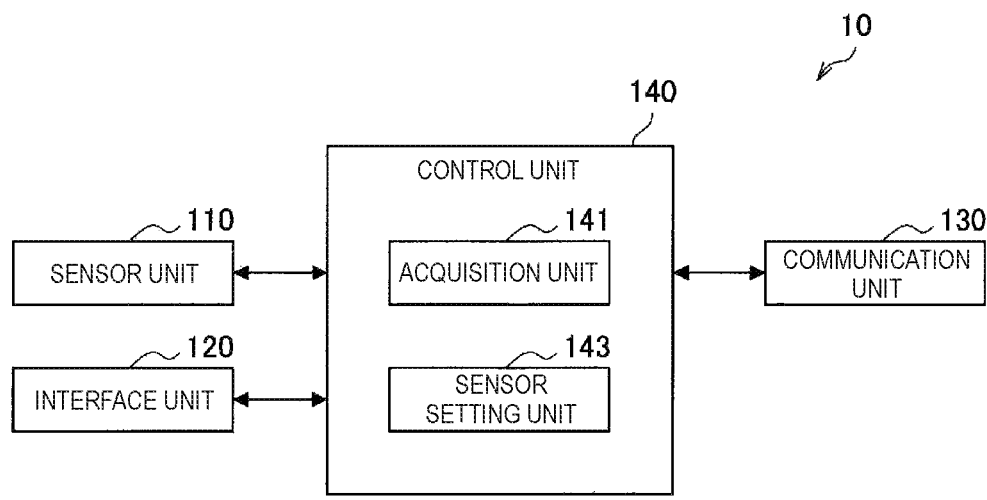
FIG. 8 is a block diagram illustrating an example of a logical configuration of the sensor device 10 according to the embodiment.

FIG. 8 is a block diagram illustrating an example of a logical configuration of the sensor device 10 according to the present embodiment. As illustrated in FIG. 8, the sensor device 10 includes a sensor unit 110, an interface unit 120, a communication unit 130, and a control unit 140.

The sensor unit 110 has a function of sensing information relating to a target object. In one example, the sensor unit 110 may include an inertia sensor such as an acceleration sensor or a gyro sensor. In addition, the sensor unit 110 may include a biological information measuring unit such as a myoelectric sensor, a neural sensor, a pulse sensor, or a body temperature sensor. In addition, the sensor unit 110 may include a vibration sensor, a geomagnetic sensor, or the like. The sensor unit 110 outputs sensor information to the control unit 140.

The interface unit 120 is an interface with the sensor fixture 21 to which the sensor device 10 is attached. In one example, the interface unit 120 includes the terminal 13 and the switch 14. In one example, the interface unit 120 outputs information regarding the electric signal flowing between the terminal 13 and the terminal 22, to the control unit 140. In addition, the interface unit 120 outputs information, r regarding depression of the switch 14 performed by the concavo-convex portion 23, to the control unit 140.

The communication unit 130 is a communication module configured to transmit and receive data to and from an external device. In one example, the communication unit 130 transmits and receives data to and from the smartphone 30. The communication unit 130 directly communicates with the smartphone 30 using a communication scheme such as a wireless local area network (LAN), Wireless Fidelity (Wi-Fi, registered trademark), infrared communication, and Bluetooth (registered trademark), or indirectly communicates with the smartphone 30 via another communication node such as a network access point. The communication unit 130 may perform wired communication with an external device using a communication scheme such as a wired LAN.

For example, the communication unit 130 transmits sensor information sensed by the sensor unit 110 to the smartphone 30. In addition, it is also possible for the communication unit 130 to transmit information acquired by an acquisition unit 141 (to be described later) of the control unit 140, to the smartphone 30.

The control unit 140 functions as an arithmetic processing device and a control device, and controls the overall operation in the sensor device 10 in accordance with various programs. As illustrated in FIG. 8, the control unit 140 functions as the acquisition unit 141 and a sensor setting unit 143.

In the case where the sensor device 10 is attached to the target object 20 via the sensor fixture 21, the acquisition unit 141 acquires information on the basis of a mode of the sensor fixture 21. For example, the acquisition unit 141 has a function of acquiring information indicating an attachment attitude of the sensor device 10 to the target object 20. In addition, the acquisition unit 141 may have a function of acquiring information indicating an attachment position of the sensor device 10 to the target object 20. Note that, hereinafter, the information indicating an attachment attitude may also be referred to as attachment attitude information, and the information indicating an attachment position may also be referred to as attachment position information. In addition, hereinafter, a set of the attachment attitude information and the attachment position information may also be referred to as attachment information. Therefore, the acquisition unit 141 may acquire the attachment information including the attachment attitude information and the attachment position information.

For example, the attachment attitude information may be information regarding axes of the sensor with respect to a predetermined axis (such as a shaft) associated with the target object 20 (such as information regarding positive/negative of x, y, and z axes), or may be information regarding rotation with respect to a predetermined coordinate axis (such as a rotation matrix). In addition, in the case where the attachment attitude via the sensor fixture 21 includes only one attachment attitude, the attachment attitude information may serve as identification information for specifying the sensor fixture 21. In the case where attachment attitudes via respective sensor fixtures 21 and identification information of the respective sensor fixture 21 are known, it is possible for the sensing system 1 to specify attachment attitudes.

This configuration enables the sensing system 1 to specify attachment attitudes. Therefore, it is possible to perform measurement corresponding to various attitudes.

For example, the attachment position information may be information indicating detailed parts such as a grip or a shaft of a golf club. In addition, the attachment position information may also serve as identification information for specifying the sensor fixture 21. If positions of respective sensor fixtures 21 on the target object 20 and identification information of respective sensor fixtures 21 are known, it is possible for the sensing system 1 to specify attachment positions.

In one example, the acquisition unit 141 may acquire the attachment information on the basis of electrical characteristics of the sensor fixture 21 to which the attachment portion 12 is attached. In one example, the acquisition unit 141 acquires a resistance value as the attachment information. The resistance value is obtained by flowing an electric current between the terminal 13 and the terminal 22 that are in contact with each other. In addition, the sensing system 1 may specify the sensor fixture 21 to which the attachment portion 12 is attached from the resistance value acquired by the acquisition unit 141.

In one example, the acquisition unit 141 may acquire the attachment information on the basis of a physical shape of the sensor fixture 21 to which the attachment portion 12 is attached. In one example, when the sensor device 10 is screwed into the sensor fixture 21, the acquisition unit 141 acquires a concavo-convex pattern (e.g., the number of convex portions, interval between the convex portions, and the heights of the convex portions) of the concavo-convex portion 23 as the attachment information. The concavo-convex pattern is obtained from the switch 14 pressed by the concavo-convex portion 23. In addition, the sensing system 1 may specify the sensor fixture 21 to which the attachment portion 12 is attached, from the concavo-convex pattern acquired by the acquisition unit 141.

In any way, it is possible for the sensing system 1 to automatically acquire the attachment information including the attachment attitude information and the attachment position information when the sensor device 10 is attached to the target object 20 via the sensor fixture 21. This configuration does not require a user to input the attachment attitude information, the attachment position information, or the like, for example. Therefore, it is possible to improve convenience of the user.

The sensor setting unit 143 has a function of configuring settings of the sensor unit 110. The sensor setting unit 143 may configure the settings of the sensor unit 110 on the basis of information acquired by the acquisition unit 141.

For example, the sensor setting unit 143 sets resolution (sampling frequency) of sensing to be performed by the sensor unit 110, on the basis of attachment attitude information acquired by the acquisition unit 141. For example, on the basis of attachment attitude information, the sensor setting unit 143 may set high resolution to an axis that matches a movement direction in which large movement tends to occur (such as swing direction of golf club), and set low resolution to the other axes. This configuration enables the sensor device 10 to adjust data amounts to be transmitted in accordance with an attachment attitude of the sensor device 10.

2-3. Functional Configuration Example of Smartphone

Figure 9:
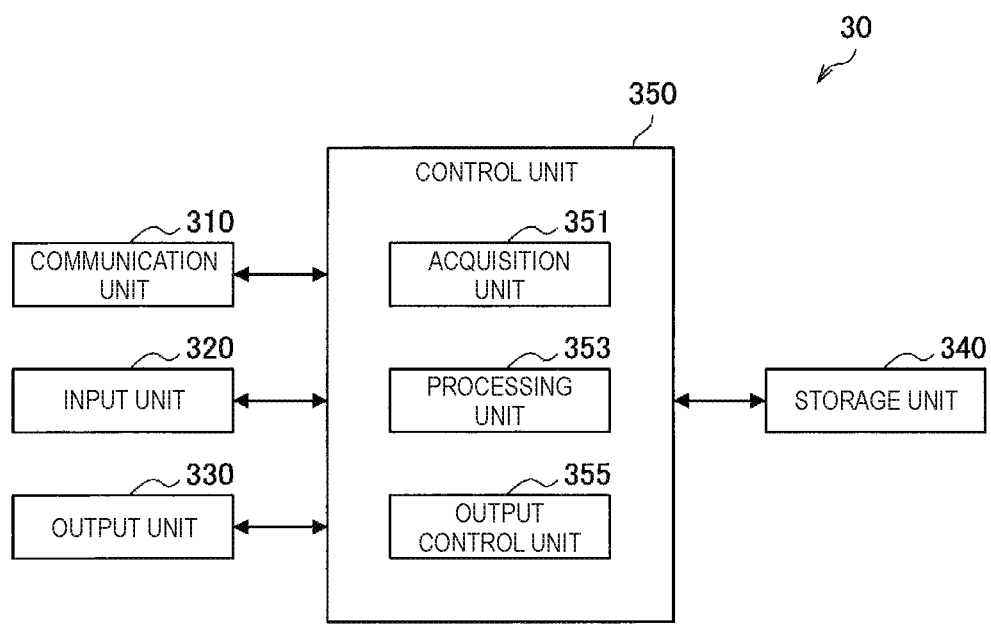
FIG. 9 is a block diagram illustrating an example of a logical configuration of a smartphone 30 according to the embodiment.

FIG. 9 is a block diagram illustrating an example of a logical configuration of the smartphone 30 according to the embodiment. As illustrated in FIG. 9, the smartphone 30 includes a communication unit 310, an input unit 320, an output unit 330, a storage unit 340, and a control unit 350.

The communication unit 310 is a communication module configured to transmit and receive data to and from an external device. In one example, the communication unit 310 transmits and receives data to and from the sensor device 10. The communication unit 310 directly communicates with the sensor device 10 using a communication scheme such as a wireless LAN, Wi-Fi, infrared communication, Bluetooth (registered trademark), or a wired LAN, or indirectly communicates with the sensor device 10 via another communication node such as a network access point.

The input unit 320 has a function of receiving operation performed by a user. In one example, the input unit 320 is implemented by a keyboard, a mouse, or the like. In addition, the input unit 320 may be implemented by a touchscreen integrated with a display device (the output unit 330).

The output unit 330 has a function of outputting information to the user in the form of video, image, audio, or the like. The output unit 330 is implemented as, in one example, a cathode ray tube (CRT) display device, a liquid crystal display device, a loudspeaker, or the like.

The storage unit 340 is a unit configured to record and reproduce data in a predetermined recording medium. In one example, the storage unit 340 stores data received from the sensor device 10 via the communication unit 310.

The control unit 350 functions as an arithmetic processing device and a control device, and controls overall operation in the smartphone 30 in accordance with various programs. As illustrated in FIG. 9, the control unit 350 functions as an acquisition unit 351, a processing unit 353, and an output control unit 355.

The acquisition unit 351 has a function of acquiring sensor information, attachment attitude information, and attachment position information from the sensor device 10 via the communication unit 310.

The processing unit 353 has a function of processing sensor information acquired by the acquisition unit 351, on the basis of attachment attitude information and attachment position information. In addition, the processing unit 353 may generate a trajectory of movement of a target object on the basis of processed sensor information.

For example, the processing unit 353 rotates sensor information on the basis of attachment attitude information such that sensor information becomes data seen from a predetermined direction with respect to the target object 20 (for example, the processing unit 353 performs coordinate transformation for rotating coordinates of a trajectory of movement obtained from sensor information). For example, the processing unit 353 may rotate sensor information by using a rotation matrix (an example of attachment attitude information). In addition, the processing unit 353 may determine a still state on the basis of sensor information, consider acceleration in the still state as a gravity direction, rotate the sensor information, and consider the sensor information in the still state as an initial position of the trajectory of movement. Note that, an object may be determined as the still state in the case where a state in which magnitude (norm) of acceleration is substantially the same as gravitational acceleration is detected, in the case where a state in which change in acceleration predetermined time before a specific movement of sports specified from vibration frequency characteristics (such as ball hitting movement in tennis) is small is detected, or in other cases.

For example, this configuration enables visualization of pieces of sensor information of a trajectory of swing of a golf club (target object 20) to which sensor devices are attached with different attachment attitudes, such that the target object 20 is seen from the same direction. This enables a user to check and compare the pieces of sensor information more efficiently.

In addition, the processing unit 353 may estimate movement information of a predetermined position on the target object 20, from sensor information on the basis of attachment position information. For example, the processing unit 353 may estimate movement information of a club head (an example of the predetermined position) of the golf club 20A (an example of the target object), from sensor information acquired by the sensor device 10B attached at the position of the sensor fixture 21B illustrated in FIG. 2. For example, the processing unit 353 uses attachment position information and information regarding the length of the golf club 20A, and performs coordinate transformation for translating coordinates obtained from sensor information into coordinate corresponding to a predetermined position on the target object 20. Therefore, it is possible for the processing unit 353 to estimate movement information at the predetermined position.

This configuration enables visualization of movement or the like at a position of a golf club (target object) hitting a ball, and it is possible to visualize various kinds of movement.

The output control unit 355 has a function of controlling the output unit 330 such that the output unit 330 outputs information. For example, the output control unit 355 may cause the output unit 330 to display a trajectory of movement of a predetermined position (such as club head of golf club) on the target object 20, which is obtained by the processing unit 353 performing coordinate transformation such as rotation or estimation of movement at the predetermined position.

2. OPERATION EXAMPLE

Figure 10:
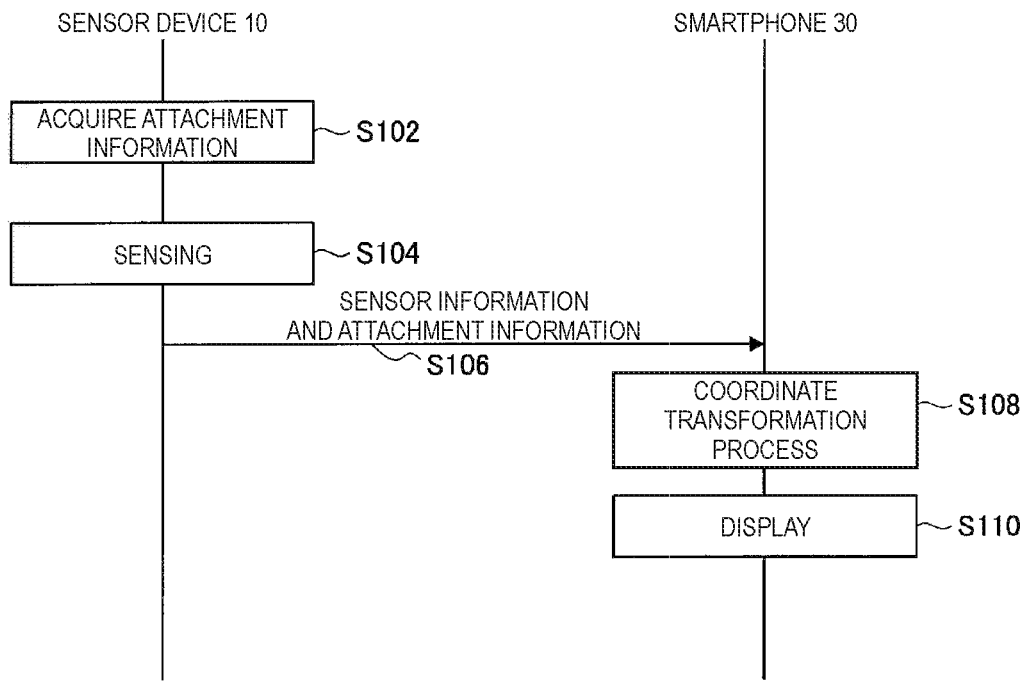
FIG. 10 is a sequence diagram illustrating an example of workflow of a sensing process performed by the sensor device 10 according to the embodiment.

The configurations of the respective devices included in the sensing system 1 according to the embodiment have been described above. Next, with reference to FIG. 10, an operation process example of the sensing system 1 according to the embodiment will be described. FIG. 10 is a sequence diagram illustrating an example of workflow of a sensing process performed by the sensor device 10 according to the embodiment.

First, as illustrated in FIG. 10, the acquisition unit 141 of the sensor device 10 acquires attachment information including attachment attitude information and attachment position information (Step S102). Here, the sensor setting unit 143 of the sensor device 10 may configure settings of the sensor unit 110. Next, the sensor unit 110 of the sensor device 10 senses movement of the target object 20 (Step S104).

Subsequently, the communication unit 130 of the sensor device 10 transmits the sensor information acquired through sensing performed by the sensor unit 110 and the attachment information acquired by the acquisition unit 141, to the smartphone 30 (S106).

A coordinate transformation process (rotation for obtaining data seen from a predetermined direction, and translation to a predetermined position) is performed on the sensor information by the processing unit 353 of the smartphone 30 that has received the sensor information and the attachment information (S108). Next, the output unit 330 of the smartphone 30 displays the sensor information subjected to the coordinate transformation, as the trajectory illustrated in FIG. 4, for example (S110).

4. MODIFICATIONS

The embodiment of the present disclosure has been described above. Next, some modifications of the embodiment will be described. Note that, the modifications to be described below may be applied to the embodiment separately, or may be applied to the modification in combination. In addition, the modifications may be applied instead of the configurations described in the embodiment, or may be applied in addition to the configurations described in the embodiment.

4-1. First Modification

In the above described embodiment, the example in which the processing unit of the smartphone processes sensor information on the basis of information received from the sensor device has been described. However, it is also possible for a device other than the smartphone to process sensor information.

Figure 11:
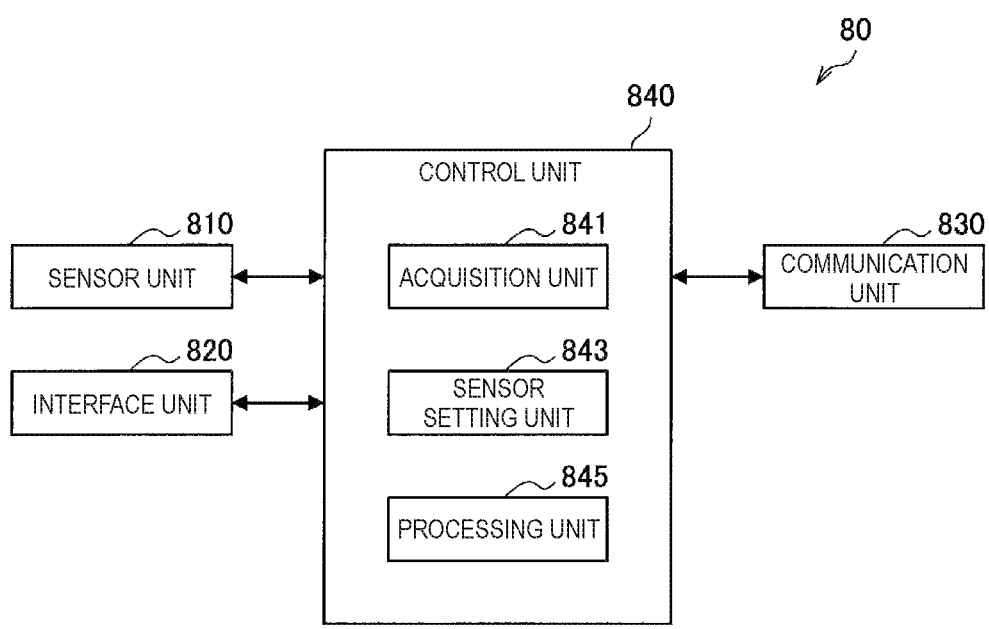
FIG. 11 is an explanatory diagram illustrating a configuration example of a sensor device including a processing unit.

For example, it is possible for the sensor device to include the processing unit and perform the above described process. FIG. 11 is an explanatory diagram illustrating a configuration example of a sensor device in the case where the sensor device includes the processing unit. A sensor device 80 illustrated in FIG. 11 includes a sensor unit 810, an interface unit 820, a communication unit 830, and a control unit 840. Among the above listed structural elements, configurations of the sensor unit 810, the interface unit 820, and the communication unit 830 are similar to the configurations of the sensor unit 110, the interface unit 120, and the communication unit 130 described with reference to FIG. 8. Therefore, the description of configurations of the sensor unit 810, the interface unit 820, and the communication unit 830 is omitted.

The control unit 840 functions as an arithmetic processing device and a control device, and controls overall operation in the sensor device 80 in accordance with various programs. As illustrated in FIG. 11, the control unit 840 functions as an acquisition unit 841, a sensor setting unit 843, and a processing unit 845. Among the above listed structural elements, functions of the acquisition unit 841 and the sensor setting unit 843 are similar to the functions of the acquisition unit 141 and the sensor setting unit 143 described with reference to FIG. 8. Therefore, the description of the functions of the acquisition unit 841 and the sensor setting unit 843 is omitted.

The processing unit 845 has a function of processing sensor information acquired through sensing performed by the sensor unit 810, on the basis of attachment attitude information and attachment position information that are acquired by the acquisition unit 841. For example, the processing unit 845 may perform a process of rotating sensor information or a process of estimating movement information of a predetermined position on a target object from the sensor information, in a way similar to the processing unit 353 of the smartphone 30 that has been described with reference to FIG. 9.

In addition, it is also possible for the sensing system to further include a server configured to communicate with the smartphone directly or via a communication network, and the server may process sensor information. The server may rotate the sensor information, may estimate movement information of a predetermined position on a target object from the sensor information, or may perform a process based on sensor information regarding a plurality of users.

For example, the server may receive pieces of sensor information from a plurality of smartphones owned by a plurality of users, accumulate the pieces of sensor information, and perform a statistical process on the pieces of sensor information. For example, the server that has received a piece of sensor information of a certain user from a smartphone may compare the received piece of sensor information with an accumulated piece of sensor information regarding another user, generate advice information for supporting his/her improvement, transmit the advice information to the smartphone, and cause the smartphone to display the advice information.

4-2. Second Modification

In the above described embodiment, the example in which the acquisition unit 141 of the sensor device 10 acquires attachment information has been described. However, the present disclosure is not limited thereto. By using the mechanism described in the above embodiment, it is possible for the acquisition unit 141 to acquire various kinds of information.

In one example, it is possible to configure settings for identification of individuals in a team, with regard to the terminal 22 and/or the concavo-convex portion 23 of the sensor fixture 21. In this case, the acquisition unit 141 may acquire information indicating a team of the user to which the sensor device is attached, a position (e.g., offense or defense) in a game of the user to which the sensor device is attached, or a uniform number of the user to which the sensor device is attached, from the resistance value and/or the concavo-convex pattern.

In addition, in one example, the acquisition unit 141 may acquire information indicating that the sensor device is not attached. In addition, the acquisition unit 141 may acquire information indicating a target object to which the sensor device is attached. In one example, the acquisition unit 141 may acquire information indicating that the sensor device is attached to a user, equipment such as a golf club, a charger, a device for calibrating the sensor device 10, a shipping inspection machine in a factory, or the like.

In addition, it is also possible for the acquisition unit 141 to acquire information indicating types of sports games using the target object 20. This configuration enables the smartphone 30 that has received information indicating a type of a sports game from the sensor device 10 to automatically start an application corresponding to the type of sports game. In addition, the respective sports games have different appropriate directions with regard to the above described predetermined direction of visualization. For example, in the case where the type of sports game is golf, visualization of data seen from a front direction of a user may be appropriate. Meanwhile, respective sports games may have different predetermined directions. According to the above described configuration, it is also possible to select a predetermined direction of visualization in accordance with types of sports games.

In such a case, it is possible for the sensor fixture 21 to have modes (electrical characteristics or physical characteristics) corresponding to various types of information pieces as described above.

In addition, the various types of information pieces acquired by the acquisition unit 141 may be information set by users. In this case, the sensor fixture 21 may have modes corresponding to user input. For example, it is possible for the concavo-convex portion 23 to have a mechanism that a user can slide. When the user slides the concavo-convex portion 23, a mode of the sensor fixture 21 changes, and information is set. This configuration enables the sensing system to acquire more various types of information, and perform various ty7upes of processes based on such information.

5. HARDWARE CONFIGURATION EXAMPLE

Figure 12:
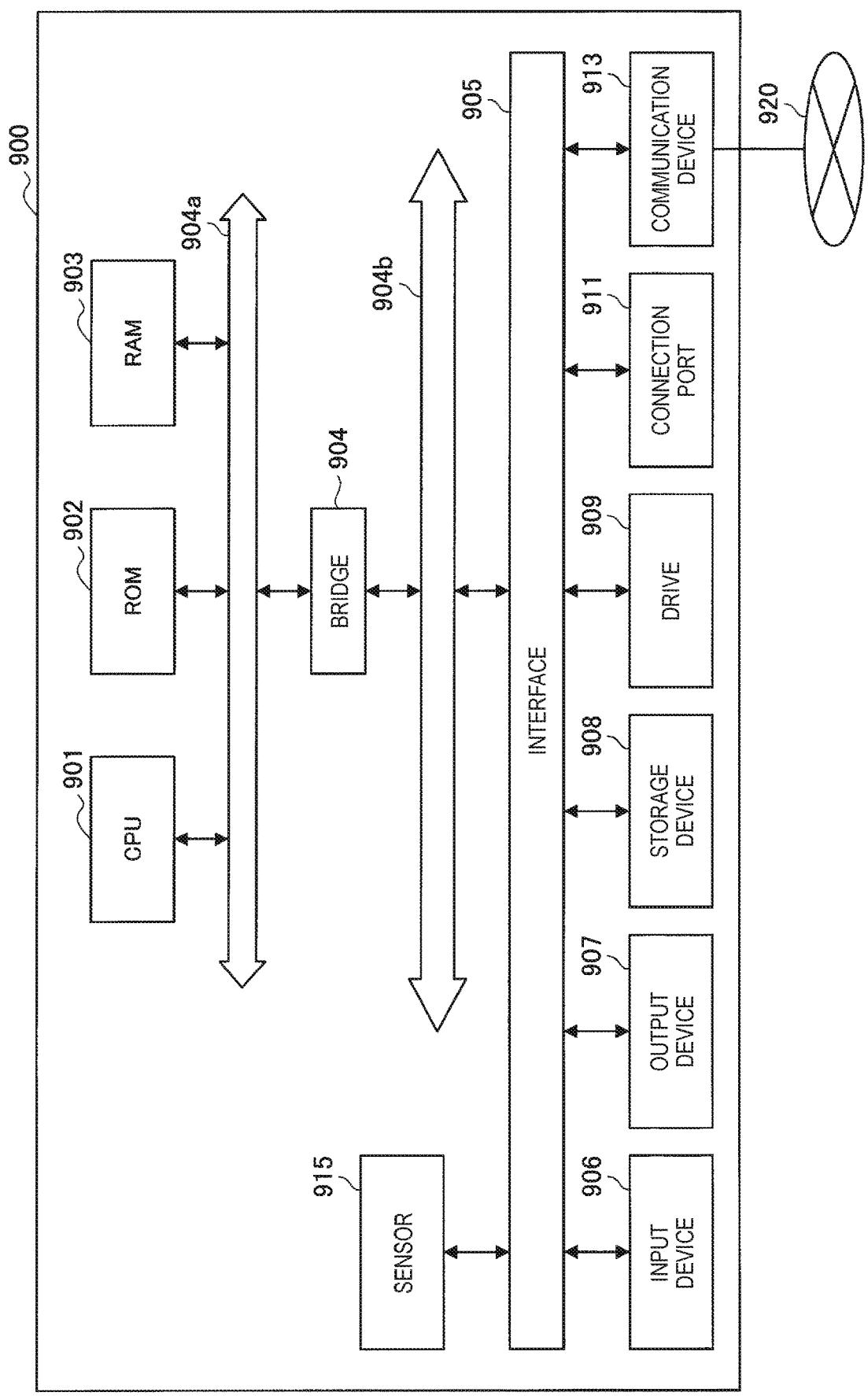
FIG. 12 is a block diagram illustrating an example of a hardware configuration of an information processing device according to the embodiment.

Last of all, with reference to FIG. 12, a hardware configuration of the information processing device according to the embodiment will be described. FIG. 12 is a block diagram illustrating an example of the hardware configuration of the information processing device according to the embodiment. Note that, the information processing device 900 illustrated in FIG. 12 may be implemented, in one example, as the sensor device 10, the smartphone 30, or the sensor device 80 illustrated in FIG. 8. 9, or 11, respectively. The information processing performed by the sensor device 10, the smartphone 30, or the sensor device 80 according to the embodiment is achieved by cooperation of software and hardware as described below.

As illustrated in FIG. 12, the information processing device 900 includes a central processing unit (CPU) 901, read only memory (ROM) 902, random access memory (RAM) 903, and a host bus 904*a*. In addition, the information processing device 900 includes a bridge 904, an external bus 904*b*, an interface 905, an input device 906, an output device 907, a storage device 908, a drive 909, a connection port 911, a communication device 913, and a sensor 915. The information processing device 900 may include a processing circuit such as a DSP or an ASIC instead of or in addition to the CPU 901.

The CPU 901 functions as an arithmetic processing device and a control device to control all operating processes in the information processing device 900 in accordance with various kinds of programs. In addition, the CPU 901 may be a microprocessor. The ROM 902 stores programs, operation parameters, and the like used by the CPU 901. The RAM 903 transiently stores programs used when the CPU 901 is executed, and parameters or the like that change as appropriate when executing such programs. The CPU 901 may be configured as, in one example, the control unit 140 illustrated in FIG. 8, the control unit 350 illustrated in FIG. 9, and the control unit 840 illustrated in FIG. 11.

The CPU 901, the ROM 902, and the RAM 903 are connected to each other through the host bus 904*a* including a CPU bus and the like. The host bus 904*a* is connected, via the bridge 904, to the external bus 904*b* such as a peripheral component interconnect/interface (PCI) bus. Note that, the host bus 904*a*, the bridge 904, and the external bus 904*b* are not necessarily configured as a separate component, but their functions may be incorporated into in a single bus.

The input device 906 is implemented as a device through which a user inputs information, such as a mouse, a keyboard, a touchscreen, a button, a microphone, a switch, or a lever. In addition, the input device 906 may be a remote control device using infrared ray or other electric waves, or may be externally connected device, such as a cellular phone or a PDA operable in response to operation of the information processing device 900. Furthermore, the input device 906 may include an input control circuit or the like that is configured to generate an input signal on the basis of information input by the user using the aforementioned input mechanism and to output the generated input signal to the CPU 901. The user of the information processing device 900 is capable of inputting various types of data to the information processing device 900, or may instruct the information processing device 900 to perform a processing operation, by operating the input device 906. The input device 906 may be configured as, in one example, the input unit 320 illustrated in FIG. 9.

The output device 907 is configured as a device capable of issuing visual or auditory notification of the acquired information to the user. An example of such a device includes a display device such as a CRT display device, a liquid crystal display device, a plasma display device, an EL display device, and a lamp, a sound output device such as a loudspeaker or headphones, and a printer device. The output device 907 outputs, for example, results acquired by various processes performed by the information processing device 900. Specifically, the display device visually displays results acquired through various processes performed by the information processing device 900 in various formats such as a text, image, table, and graph. On the other hand, the sound output device converts audio signals including reproduced sound data, audio data, and the like into analog signals and audibly outputs them. The aforementioned display device and sound output device may be configured as, for example, the output unit 330 illustrated in FIG. 9.

The storage device 908 is a device for data storage configured as an example of a storage unit of the information processing device 900. In one example, the storage device 908 is implemented as a magnetic storage device such as an HDD, a semiconductor storage device, an optical storage device, a magneto-optical storage device, or the like. The storage device 908 may include a storage medium, a recording device configured to record data on the storage medium, a read-out device configured to read out data from the storage medium, a deletion device configured to delete data recorded on the storage medium, and the like. The storage device 908 stores programs and various types of data executed by the CPU 901, various types of data acquired from an outside, and the like. The storage device 908 may be configured as, for example, the storage unit 340 illustrated in FIG. 9.

The drive 909 is a reader/writer for a recording medium, and is incorporated in or externally attached to the information processing device 900. The drive 909 reads out information recorded on a removable recording medium that is mounted such as a magnetic disk, an optical disc, a magneto-optical disk, or semiconductor memory, and outputs the information to the RAM 903. The drive 909 also writes information to the removable storage medium.

The communication port 911 is an interface for connection to an external device, and is, for example, a connection port for connection to an external device capable of transmitting data via a USB (Universal Serial Bus). The connection port 911 may be configured as, for example, the interface unit 120 illustrated in FIG. 8.

The communication device 913 is, for example, a communication interface implemented by a communication device or the like for connection with a network 920. The communication device 913 is, for example, a communication card or the like for a wired or wireless local area network (LAN), long term evolution (LTE), Bluetooth (registered trademark), or wireless USB (WUSB). In addition, the communication device 913 may be a router for optical communication, a router for asymmetric digital subscriber line (ADSL), various communication modems, or the like. In one example, the communication device 913 is capable of transmitting and receiving signals and the like to and from the Internet or another communication device, for example, in accordance with a predetermined protocol such as TCP/IP or the like. The communication device 913 may be configured as, for example, the communication unit 130 illustrated in FIG. 8, the communication unit 310 illustrated in FIG. 9, and the communication unit 830 illustrated in FIG. 11.

Note that, the network 920 is a wired or wireless transmission path through which information is transmitted from devices connected with the network 920. In one example, the network 920 may include a public circuit network such as the Internet, a telephone circuit network, and a satellite communication network, various local area networks (LANs) including Ethernet (registered trademark), a wide area network (WAN), and the like. In addition, the network 920 may include a dedicated circuit network such as an internet protocol-virtual private network (IP-VPN).

The sensor 915 is various sensors such as an acceleration sensor, a gyro sensor, a geomagnetic sensor, an optical sensor, a sound sensor, a ranging sensor, and a force sensor. The sensor 915 acquires information regarding the state of the information processing device 900 itself such as the attitude and moving speed of the information processing device 900, information regarding a surrounding environment of the information processing device 900 such as brightness and noise around the information processing device 900. In addition, the sensor 915 may include a GPS sensor configured to receive a GPS signal and measuring the latitude, longitude, and altitude of the device. The sensor 915 may be configured as, for example, the sensor unit 110 illustrated in FIG. 8, and the sensor unit 810 illustrated in FIG. 11.

An example of the hardware configuration capable of implementing the functions of the information processing device 900 according to the present is illustrated above. The respective structural elements described above may be implemented using versatile members, or may be implemented by hardware pieces that are specific to the functions of the respective structural elements. Accordingly, it is possible to change a hardware configuration to be used appropriately depending on the technical level when carrying out the embodiments.

Note that, it is possible to create a computer program for implementing each of the functions of the information processing device 900 according to the embodiment, and mount them in a PC or the like. Furthermore, it is also possible to provide a computer-readable recording medium on which such a computer program is stored. The recording medium is, for example, a magnetic disc, an optical disc, a magneto-optical disc, a flash memory, or the like. The computer program may be distributed, for example, through a network without using the recording medium.

6. CONCLUSION

As described above, according to the present disclosure, the sensor device acquires its own attachment attitude on the basis of a mode of the sensor fixture. Therefore, it is possible to perform measurement corresponding to various types pf attachment attitudes.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, it may not be necessary to chronologically execute respective steps according to the above described embodiment, in the order described in the sequence diagrams. For example, the respective steps in the processes according to the above described embodiment may be processed in the order different from the order described in the sequence diagrams, and may also be processed in parallel.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A sensing system including:

a sensor fixture that has a mode corresponding to an attachment attitude to a target object; and a sensor device configured to be attached with the attachment attitude to the target object via the sensor fixture, the sensor device including a sensor unit configured to sense information regarding the target object, and an acquisition unit configured to acquire information indicating the attachment attitude on a basis of the mode of the sensor fixture.

(2)

The sensing system according to (1), in which the sensor device further includes a communication unit configured to transmit sensor information sensed by the sensor unit and information acquired by the acquisition unit, to another device.

(3)

The sensing system according to (1) or (2), in which the sensor device further includes a sensor setting unit configured to make a setting of the sensor unit on a basis of information acquired by the acquisition unit.

(4)

The sensing system according to (3), in which the sensor setting unit makes a setting of resolution of sensing to be performed by the sensor unit.

(5)

The sensing system according to any one of (1) to (4), in which the acquisition unit acquires information on a basis of an electrical characteristic of the sensor fixture.

(6)

The sensing system according to any one of (1) to (5), in which the acquisition unit acquires information on a basis of a physical form of the sensor fixture.

(7)

The sensing system according to any one of (1) to (6), in which the sensor fixture further has a mode corresponding to an attachment position on the target object.

(8)

The sensing system according to any one of (1) to (7), in which the sensor fixture further has a mode corresponding to input performed by a user.

(9)

The sensing system according to any one of (1) to (8), in which the target object is an object to be used by a living being.

(10)

The sensing system according to any one of (1) to (9), in which the sensor device further includes a processing unit configured to process sensor information sensed by the sensor unit, on a basis of information acquired by the acquisition unit.

(11)

The sensing system according to (10), in which the processing unit performs a process of rotating the sensor information on a basis of the information indicating the attachment attitude acquired by the acquisition unit.

(12)

A sensor device including:

a sensor unit configured to sense information regarding a target object; and an acquisition unit configured to acquire information indicating attachment attitude to the target object, from a sensor fixture, in which the sensor device is configured to be attached with the attachment attitude to the target object via the sensor fixture.

(13)

A sensor fixture that has a mode corresponding to an attachment attitude to a target object, and that attaches a sensor device with the attachment attitude to the target object.

REFERENCE SIGNS LIST 1 sensing system
5 communication network
10 sensor device
11 main body portion
12 attachment portion
13 terminal
14 switch
20 target object
21 sensor fixture
22 terminal
23 concavo-convex portion
30 information processing device
100 device
102 part
110 sensor unit
120 interface unit
130 communication unit
140 control unit
141 acquisition unit
143 sensor setting unit
310 communication unit
320 input unit
330 output unit
340 storage unit
350 control unit
351 acquisition unit
353 processing unit
355 output control unit

The invention claimed is:

1. A sensing system, comprising:
a sensor fixture that comprises a first mode, wherein
the first mode corresponds to an attachment attitude of the sensor fixture; and
a sensor device attachable to a target object via the sensor fixture, wherein
the sensor device is attachable based on the attachment attitude of the sensor fixture,
each axis of the sensor device has a different relation with respect to the target object based on the attachment attitude of the sensor fixture, and
the sensor device includes:
an acquisition unit configured to acquire first attachment information based on a physical shape of the sensor fixture, wherein the acquired first attachment information indicates the attachment attitude of the sensor fixture on the target object;
a sensor setting unit configured to set a resolution of a sensing operation based on the attachment attitude of the sensor fixture on the target object, wherein at least one axis of the sensor device is set to have a different resolution compared to other axes of the sensor device based on the set resolution; and
a sensor unit configured to execute the sensing operation to detect sensor information regarding the target object, wherein the execution of the sensing operation is based on the set resolution.

2. The sensing system according to claim 1, wherein the sensor device further includes a communication unit configured to transmit the sensor information and the acquired first attachment information to a first device.

3. The sensing system according to claim 1, wherein the sensor setting unit is further configured to set the sensor unit based on the acquired first attachment information.

4. The sensing system according to claim 1, wherein
the sensor fixture further comprises a second mode, and
the second mode corresponds to an attachment position of the sensor fixture on the target object.

5. The sensing system according to claim 1, wherein the sensor fixture further comprises a second mode corresponding to a user input.

6. The sensing system according to claim 1, wherein the target object is an object that is usable by a living being.

7. The sensing system according to claim 1, wherein the sensor device further includes a processing unit configured to process the sensor information, sensed by the sensor unit, based on the acquired first attachment information.

8. The sensing system according to claim 7, wherein
the processing unit is further configured to transform the sensor information based on the acquired first attachment information.

9. The sensing system according to claim 1, wherein the acquisition unit is further configured to acquire second attachment information based on an electrical characteristic of the sensor fixture.

10. The sensing system according to claim 9, wherein the acquired second attachment information corresponds to a resistance value obtained based on a flow of current between the sensor fixture and the sensor device.

11. A sensor device, comprising:
an acquisition unit configured to acquire attachment information based on a physical shape of a sensor fixture, wherein
the sensor device is attachable to a target object via the sensor fixture,
the sensor device is attachable based on an attachment attitude of the sensor fixture,
each axis of the sensor device has a different relation with respect to the target object based on the attachment attitude of the sensor fixture,
the sensor fixture comprises a plurality of convex portions, and
the acquired attachment information indicates the attachment attitude of the sensor fixture on the target object;
a sensor setting unit configured to set a resolution of a sensing operation based on the attachment attitude of the sensor fixture on the target object, wherein at least one axis of the sensor device is set to have a different resolution compared to other axes of the sensor device based on the set resolution; and
a sensor unit configured to execute the sensing operation to detect sensor information regarding the target object, wherein the execution of the sensing operation is based on the set resolution.

12. A sensor fixture, comprising:
a plurality of convex portions; and
circuitry configured to attach a sensor device to a target object, wherein
the sensor device is attached to the target object based on an attachment attitude of the sensor fixture,
each axis of the sensor device has a different relation with respect to the target object based on the attachment attitude of the sensor fixture,
the sensor fixture comprises a mode corresponding to the attachment attitude,
the sensor device acquires attachment information based on a physical shape of the sensor fixture,
the acquired attachment information indicates the attachment attitude of the sensor fixture on the target object,
the sensor device sets a resolution of a sensing operation based on the attachment attitude of the sensor fixture on the target object, and executes the sensing operation to detect sensor information regarding the target object,
at least one axis of the sensor device is set to have a different resolution compared to other axes of the sensor device, and
the execution of the sensing operation is based on the set resolution.

* * * * *